United States Patent [19]

Bauman

[11] Patent Number: 5,353,460
[45] Date of Patent: Oct. 11, 1994

[54] POWER DRIVEN TOOTHBRUSH

[75] Inventor: Gary C. Bauman, Ridgewood, N.J.

[73] Assignee: Ohio Health Care Products, Inc., North Bergen, N.J.

[21] Appl. No.: 125,784

[22] Filed: Sep. 24, 1993

[51] Int. Cl.⁵ .................. A61C 17/34; A46B 13/02
[52] U.S. Cl. ............................ 15/22.1; 15/28; 74/70
[58] Field of Search ............ 15/22.1, 22.2, 22.4, 15/28; 310/50, 80; 74/25, 48, 49, 70

[56] References Cited

U.S. PATENT DOCUMENTS

| | | |
|---|---|---|
| 2,598,275 | 3/1952 | Lakin . |
| 2,601,567 | 2/1952 | Steinberg . |
| 4,048,690 | 11/1977 | Wolfson . |
| 4,274,173 | 1/1981 | Cohen . |
| 4,320,774 | 7/1982 | Rogers . |
| 4,338,957 | 6/1982 | Meibauer . |
| 4,727,894 | 4/1988 | Meibauer . |
| 4,766,630 | 3/1988 | Hegemann . |
| 5,077,855 | 3/1992 | Ambasz . |
| 5,177,826 | 1/1993 | Vrignaud et al. . |

Primary Examiner—Edward L. Roberts
Attorney, Agent, or Firm—James & Franklin

[57] ABSTRACT

A hand-held power driven toothbrush carries a pair of exposed brush elements and self-contained driving means effective to directly drive one of said brush elements in oscillation, with linkage between the brush elements such that the second brush element is also oscillated, the two brush elements preferably being oscillated in opposite directions.

16 Claims, 3 Drawing Sheets

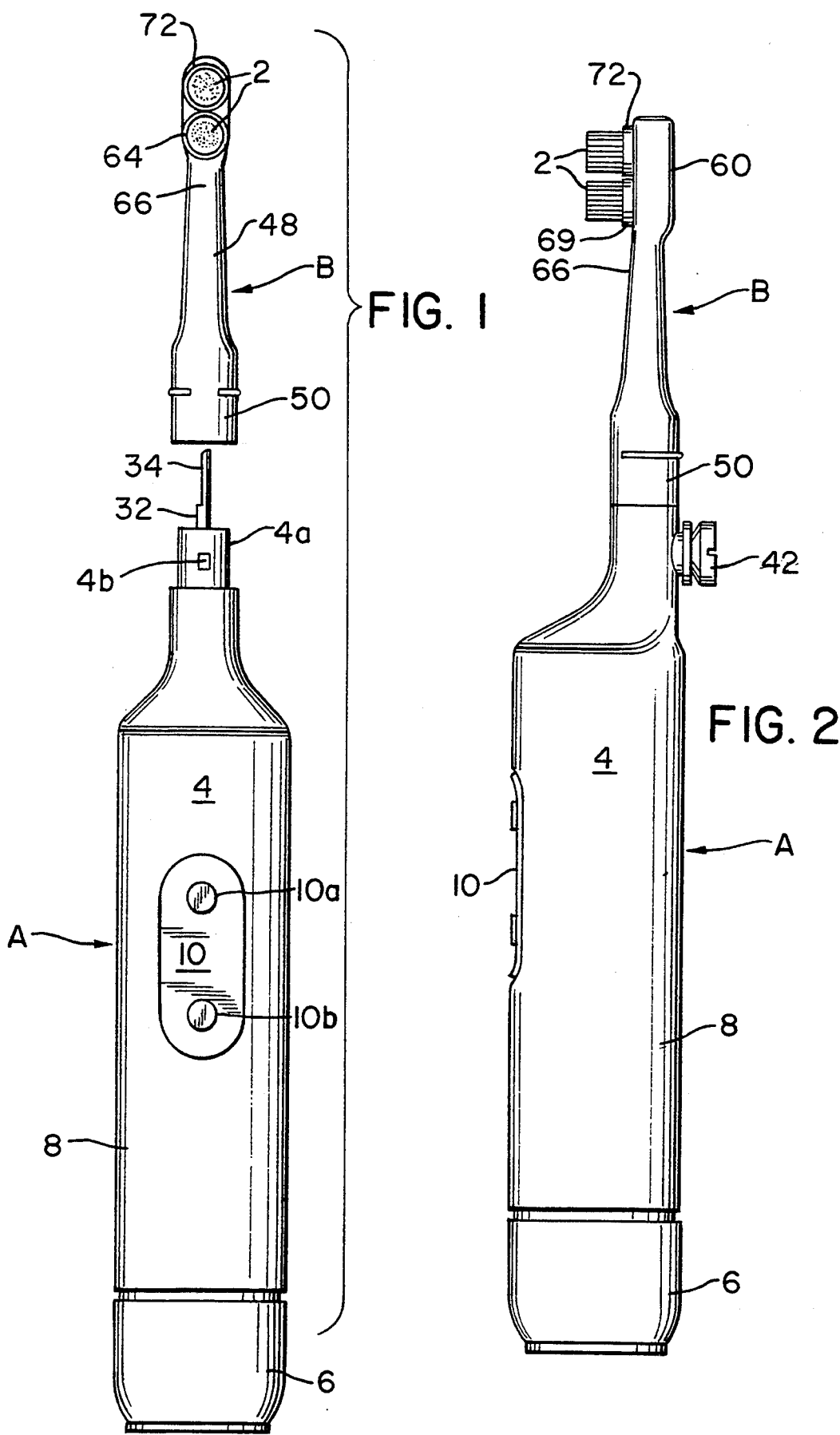

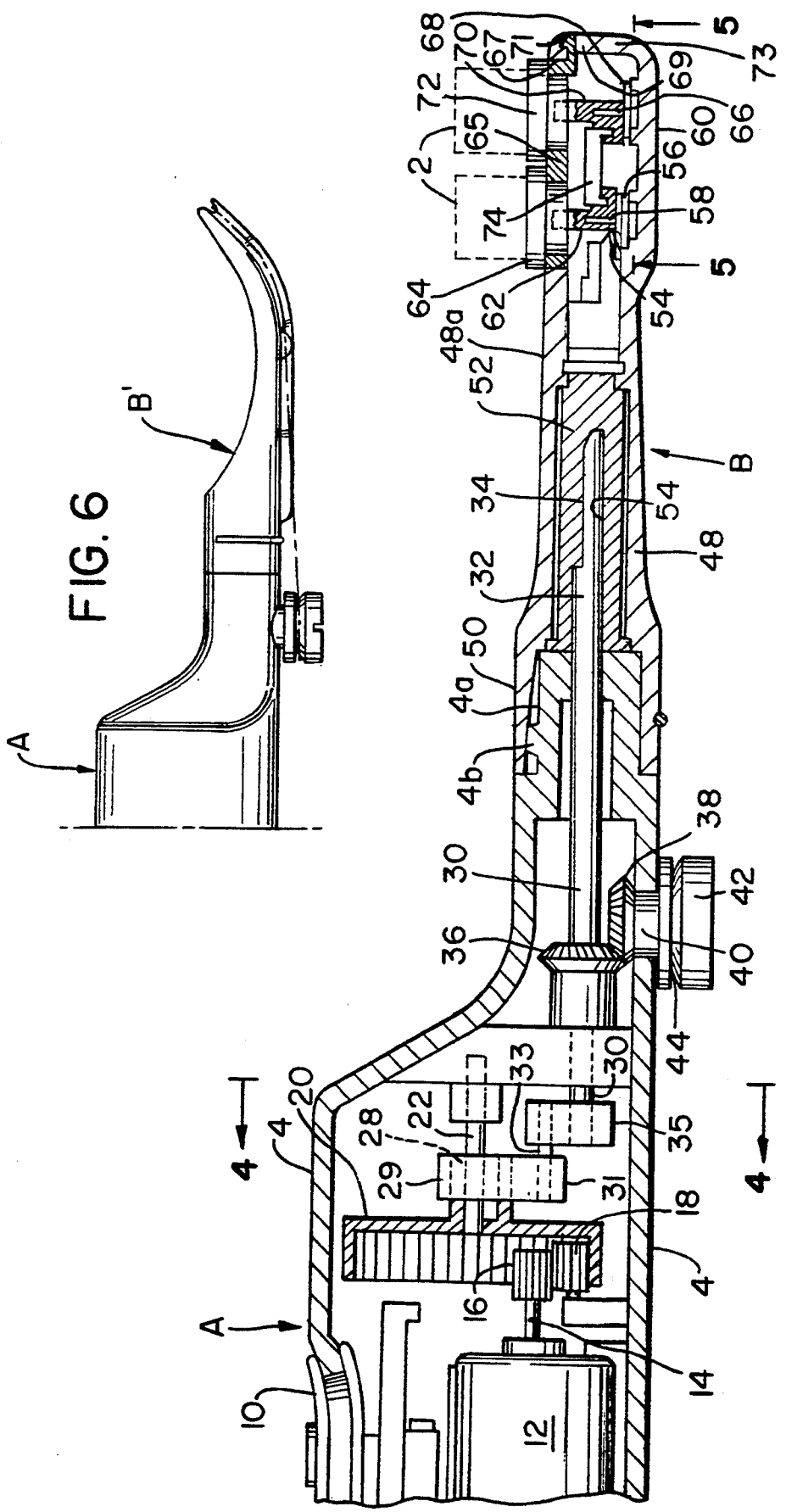

POWER DRIVEN TOOTHBRUSH

BRIEF SUMMARY OF THE INVENTION

The present invention relates to a motor driven toothbrush in which the brush elements are driven in rotary oscillation, and preferably in opposite directions respectively, by means of an exceptionally effective driving arrangement.

The need for a power driven toothbrush has been long recognized, and many suggestions have been made as to how such a device should be constructed. The requirements for such a device may be simply stated—it should be light and self-contained so as to be easily manually manipulated, the brush elements must be driven into prophylactically optimum brushing motion, the parts must be sturdy and reliable, and the part inserted into the user's mouth must be small and appropriately shaped—but to accomplish all of these objectives in a single structure is by no means simple, and hence the art is replete with suggested constructions.

Some of the requirements are mutually inconsistent—to make something small and light and at the same time sturdy and reliable is no mean task. In addition, obtaining optimum tooth cleaning and polishing from a motor driven brush element calls for considerable ingenuity, and prior art approaches to that objective have been less than satisfactory. Early approaches, such as those shown in Steinberg U.S. Pat. No. 2,601,567 of Jun. 24, 1952 and Lakin U.S. Pat. No. 2,598,275 of May 27, 1952 utilized single brush elements which were either rotated continuously in one direction or were swung back and forth, respectively. The desirability of utilizing more than a single driven brush element was soon realized, and devices of that nature are shown in Wolfson U.S. Pat. No. 4,048,690 of Sep. 20, 1977, Vrignaud U.S. Pat. No. 5,177,826 of Jan. 12, 1993, Hegemann U.S. Pat. No. 4,766,630 of Aug. 30, 1988, Rogers U.S. Pat. No. 4,320,774 of Mar. 23, 1982, and Ambasz U.S. Pat. No. 5,077,855 of Jan. 7, 1992. However, in none of these multiple brush elements devices are the brushes moved so as to have optimum brushing and polishing effect when hand-held for cleaning a person's teeth, nor are the driving connections to those brush elements simple, positive, and reliable while at the same time taking up very little space.

In addition, because tooth brushing is not the only prophylactic treatment for teeth, it is highly desirable that a power driven toothbrush be so constructed that, by ready replacement of one part with another, the device can be converted to another prophylactic operation on teeth, such as flossing between the teeth. The driving connection to the brush elements of a power driven toothbrush should, therefore, be such that the brushes can be readily removed from the handle portion of the device, with the handle then available to have some other part, such as a dental floss holder, attached thereto.

It is therefore a prime object of the present invention to devise a power driven toothbrush which can readily be held and manipulated by an individual and which will be effective to drive a pair of brush elements into optimum brushing movement, and to do so by means of structure which is simple, strong and reliable.

It is a further object of the present invention to provide such a device in which the power drive to the brush elements is such that the brush elements can be removed from a handle portion and some other device, preferably also power driven, can be attached, thus permitting the handle portion of the apparatus to do double duty.

BRIEF DESCRIPTION OF THE DRAWINGS

To the accomplishment of the above and to such other objects as may hereinafter appear, the present invention relates to the construction of a motor driven toothbrush as defined in the appended claims and as described in this specification, taken together with the accompanying drawings in which:

FIG. 1 is a front elevation exploded view of a preferred embodiment of the present invention with the brush-element-carrying part being separated from the handle portion of the apparatus;

FIG. 2 is a side elevational view of the toothbrush of FIG. 1 with the two parts assembled;

FIG. 3 is a cross-sectional view of a portion of the device of FIG. 2;

FIG. 6 is a view similar to FIG. 1, but on a reduced scale, showing a flossing attachment in place instead of the brush attachment.

DETAILED DESCRIPTION

Figure 4:
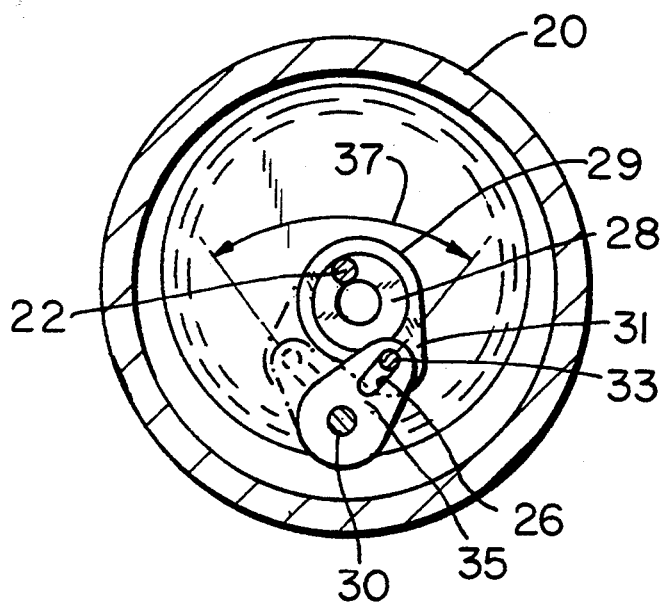
FIG. 4 is a cross-sectional view taken along the line 4—4 of FIG. 3.

The preferred embodiment of the present invention as here specifically disclosed comprises two separate parts generally designated A and B, the part A comprising the handle part and containing the power drive and batteries and the part B, removably attached to the part A, carrying the brush elements 2 which ultimately perform the tooth brushing function. The part B may be mounted on and dismounted from the part A simply by sliding it into place, and, as shown in FIG. 6, the part B carrying the brush elements 2 can be substituted for by the part B' shown in FIG. 6 adapted for holding dental floss for insertion between the user's teeth, an operation for which the brushes 2 are not prophylactically effective, and preferably imparting a back and forth movement to the floss to enhance its prophylactic effect. The details of this device as a flosser are shown and claimed in a copending application of Robert H. Meibauer entitled "Power Driven Tooth Floooser", Ser. No. 08/126,386, Sep. 24, 1993.

The handle part A which may be grasped by the user comprises a casing 4 having a removable end cap 6, the lower end 8 of the casing 4 being adapted to receive batteries when the end cap 6 is removed and to make appropriate electrical connection between those batteries, a control switch 10 exposed on the upper portion of the casing 4 and a motor 12 mounted within the casing 4 and having an output shaft 14 carrying a pinion gear 16 which meshes with a second pinion 18 rotatably mounted within the casing 4 on a fixed axis and in turn meshing with an enlarged internally toothed gear 20 rotatably mounted in the casing 4 on fixed axis 22. The gear 20 carries, preferably integral therewith, an off-center ring 28 intersected by the axis 22. Rotatably mounted on the exterior of the ring 28 is a looped portion 29 of an arm 31 which extends out radially beyond the axis of the gear 20 and which carries a pin 33 which in turn is rotatably mounted in crank arm 35 which is fast on shaft 30, the shaft 30 being journaled in the forwardly extending portion 4a of the casing 4 and extending longitudinally outwardly therefrom at 32, there terminating in an exposed flattened portion 34, preferably semicircular in cross-section. In the preferred form here specifically disclosed, adapted to be used with the powered flosser attachment B' of FIG. 6 as well as the brushing attachment B, the shaft 30 carries miter gear 36 which meshes with miter gear 38 fast on shaft 40 extending out through the casing 4 and carrying an exposed jam cleat 42 with tapered peripheral groove 44.

The switch 10 specifically here shown has two operating buttons 10a and 10b, depression of button 10a being effective to energize the motor 12 and depression of button 10b being effective to de-energize the motor 12. When the motor 12 is energized its output shaft 14 will rotate, thus rotating pinion gears 16 and 18 and internally threaded gear 20, this causing rotation of the ring 28 in an off-center fashion about the axis 22, that movement will be transferred to the arm 35 by the part 29, 31, causing that arm 35 to oscillate back and forth as indicated by the arrow 37 in FIG. 4, thus driving the shaft 30 in rotary oscillation and also imparting rotary oscillation to the exposed jam cleat 42.

Figure 5:
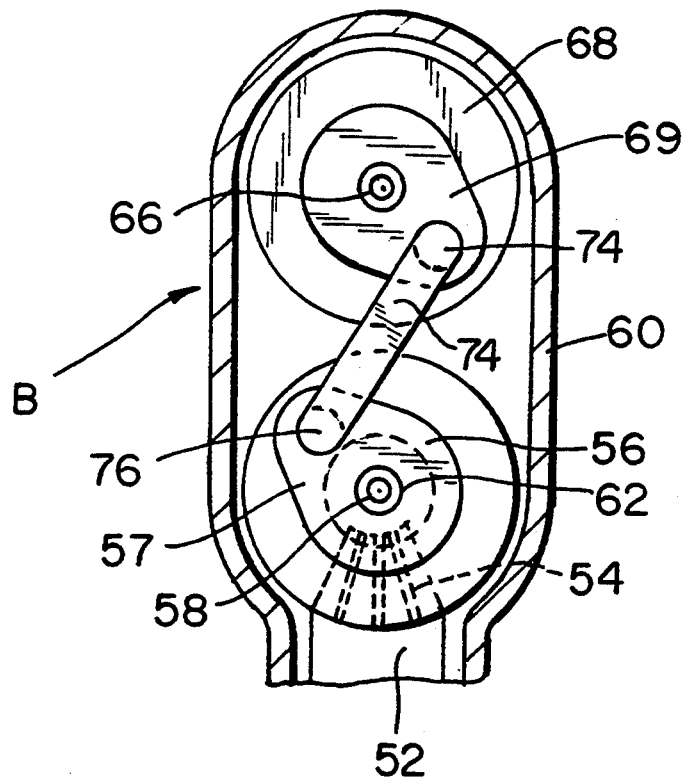
FIG. 5 is a cross-sectional view taken along the line 5—5 of FIG. 3.

The section B comprises a casing 48 having a lower cylindrical portion 50 slidably receivable over the portion 4a of the handle casing 4 with a friction fit, which fit can be enhanced by providing a projecting portion 4b on the casing portion 4a which frictionally engages the inner surface of the cylindrical portion 50 of the casing 48. As may best be seen from FIGS. 3 and 5, the casing 48 has a driven shaft 52 journaled therein, with the lower end of that shaft 52 having a preferably semicircular recess 54 into which the preferably semicircular end 34 of the drive shaft 30 is adapted to be received when the part B is placed on the part A, so that oscillatory rotation of the shaft 34 will be transmitted to the driven shaft 52. The inner end of the shaft 52 carries a miter gear portion 54 which meshes with a miter gear 56 rotatably mounted on bearing pin 58 which extends up from the bottom wall 60 of the casing 48 near its tip. An upwardly extending portion 62 of the miter gear 56 is made fast to a rotary brush carrier 64 journaled in an insert 65 in the upper wall 48a of the casing 48, which carrier 64 carries a set of bristles constituting one of the brush elements 2. Also mounted within the end portion of the casing 48, and rotatable on bearing pin 66, is a part 68 similar to the part 56, the part 68 extending up at 70 and made fast to the brush holder 72 also journaled in the casing wall 48a and carrying a set of bristles constituting the second brush element 2. The insert 65 is set into an appropriate aperture 67 in the upper casing wall 48a, and is provided with a securing protrusion 69 received in an aperture 71 in the end wall 73 of the casing 48. A link 74, best seen in FIG. 5, is pivotally connected to crank arms 56a and 68a on parts 56 and 68 respectively and extends between them, its pivotal connection 76 to crank arm 56a being to one side of the axis of rotation of the part 56 and its pivotal connection 78 to crank arm 68a being to the other side of the axis of rotation of the part 68.

Hence when the part B is put in place on the part A and the motor 12 is energized the shaft 30 will be oscillated back and forth, the shaft 52 will be similarly oscillated, the gear 56 will then be oscillated about its axis of rotation and the part 68 will be oscillated about its axis of rotation, but with the gear 56 and part 68 oscillating in opposite directions. The two brush elements 2 will therefore also be oscillated back and forth in rotary motion and in opposite directions. This will provide for optimum tooth cleaning action as a result of the oscillatory movement of the brush elements 2, the close positioning of those brush elements with respect to one another, and also preferably the fact that they are rotated in opposite directions. The driving connection from the motor 12 to the brush elements 2 is positive, yet it takes up very little space and does not require the use of any heavy or complex mechanical elements, thus enabling the device to be simple, compact, and easily held and manipulated even by a child, while at the same time the device is sturdy and reliable and hence well suited to non-professional use.

When a flosser attachment B' is mounted on the handle part A the ends of a length of floss carried thereby may be secured to the jam cleat 42 which is driven in rotary oscillation when the motor 12 is energized, thus causing the length of floss to move back and forth and produce an optimum flossing action when inserted between the teeth of the user.

While but a single embodiment of the present invention has been here specifically disclosed, it will be apparent that many variations may be made therein, all within the spirit of the invention as defined in the following claims.

I claim:

1. A power-driven toothbrush comprising a housing, first and second adjacently spaced brush elements rotatably mounted on and exposed with respect to said housing, drive means in said housing for driving said brush elements in rotary oscillation, said drive means comprising a drive shaft extending toward said brush elements, operatively drivingly connected to a first one of said brush elements, and effective to drive said first brush element into rotary oscillation, and crank linkage means between said brush elements to drive the other of said brush elements into rotary oscillation when said first brush element is driven in rotary oscillation.

2. The power-driven toothbrush of claim 1, in which said brushes oscillate about spaced substantially parallel axes respectively, said crank linkage comprising crank arms operatively connected to said brush elements and extending from the axes of rotation of their respective brush elements to opposite sides of a line between said axes, and a linkage connecting said crank arms.

3. A power-driven toothbrush comprising a housing, first and second adjacently spaced brush elements rotatably mounted on and exposed with respect to said housing, drive means in said housing for driving said brush elements in rotary oscillation, said drive means comprising a drive shaft extending toward said brush elements, operatively drivingly connected to a first one of said brush elements, and effective to drive said first brush element into rotary oscillation, and crank linkage means between said brush elements to drive the other of said brush elements into rotary oscillation opposite in direction to that of said first brush element when said first brush element is driven in rotary oscillation.

4. The power-driven toothbrush of either of claims 1 or 3, in which said housing comprises first and second separable parts, said first part containing a portion of said drive means and said second part carrying said brush elements and containing said crank linkage and another portion of said drive means.

5. The power-driven toothbrush of either of claims 1 or 3, in which said housing comprises first and second separable parts, said first part containing a first drive shaft portion which is exposed at an end of said first part, said second part carrying said brush elements, having an end adapted to be received on said end of said first part and including a second drive shaft portion exposed at said end of said second housing part and operatively connectable to said exposed portion of said first drive shaft portion at said end of said first housing part when said two housing parts are connected, said second housing part further containing gearing operatively connecting said second drive shaft portion to said first of said brush elements and also containing said crank linkage.

6. The power-driven toothbrush of claim 4, in which said brushes oscillate about spaced substantially parallel axes respectively, said crank linkage comprising crank arms operatively connected to said brush elements and extending from the axes of rotation of their respective brush elements to opposite sides of a line between said axes, and a linkage connecting said crank arms.

7. The power-driven toothbrush of claim 2, in Which said brushes oscillate about spaced substantially parallel axes respectively, said crank linkage comprising crank arms operatively connected to said brush elements and extending from the axes of rotation of their respective brush elements to opposite sides of a line between said axes, and a linkage connecting said crank arms.

8. A power-driven toothbrush attachment designed to be affixed to a base having drive means therefor, said attachment comprising an elongated housing with first and second adjacently spaced brush elements rotatably mounted thereon in exposed positions near one end thereof, the other end of said housing being adapted to be affixed to said base and having means operatively drivingly connectable to said drive means when said housing is thus affixed, said means comprising a drive shaft rotatably mounted in said housing extending from said end toward said brush elements, said drive shaft being operatively connected to a first of said brush elements and effective with said drive means to drive said first brush element into rotary oscillation, and a crank linkage between said first brush element and the other of said brush elements, thereby to drive the other of said brush elements into rotary oscillation when said first brush element is driven in rotary oscillation.

9. A power-driven toothbrush attachment designed to be affixed to a base having drive means therefor, said attachment comprising an elongated housing with first and second adjacently spaced brush elements rotatably mounted thereon in exposed positions near one end thereof, the other end of said housing being adapted to be affixed to said base and having means operatively drivingly connectable to said drive means when said housing is thus affixed, said means comprising a drive shaft rotatably mounted in said housing extending from said end toward said brush elements, said drive shaft being operatively connected to a first of said brush elements and effective with said drive means to drive said first brush element into rotary oscillation, and a crank linkage between said first brush element and the other of said brush elements, thereby to drive the other of said brush elements into rotary oscillation opposite in direction to that of said first brush element when said first brush element is driven in rotary oscillation.

10. The power-driven toothbrush of either of claims 8 or 9, in which the operative connection between said drive shaft and said first of said brush elements is a gearing connection.

11. The power-driven toothbrush of either of claims 8 or 9, in which said brush elements oscillate about spaced substantially parallel axes respectively, said crank linkage comprising crank arms operatively connected to said brush elements and extending from the axes of rotation of their respective brush elements to opposite sides of a line between said axes, and a linkage connecting said crank arms.

12. The power-driven toothbrush of claim 10, in which said brush elements oscillate about spaced substantially parallel axes respectively, said crank linkage comprising crank arms operatively connected to said brush elements and extending from the axes of rotation of their respective brush elements to opposite sides of a line between said axes, and a linkage connecting said crank arms.

13. In a power-driven tooth care device comprising a housing, a tooth care element rotatably mounted on and exposed with respect to said housing, and drive means in said housing for driving said tooth care element in rotary oscillation the improvement which comprises said drive means comprising a motor, a member rotatably mounted in said housing, means operatively connected between said motor and said member for driving the latter in rotation, said member having an off-center part, a first arm rotatably mounted on said part, an output shaft within said housing operatively connected to said tooth care element, a second arm in said housing drivingly connected to said shaft and extending radially therefrom, and an operative connection between said first and second arms for driving said second arm and said output shaft in rotary oscillation when said member is rotated by said motor.

14. The device of claim 13, in which said member and said part are integral.

15. The device of either of claims 13 or 14, in which said part has an outer circular surface and said first arm comprises a ring rotatably mounted on said outer circular surface of said part.

16. The device of either of claims 13 or 14, in which said part has an outer circular surface which substantially intersects the axis of rotation of said member and said first arm comprises a ring rotatably mounted on said outer circular surface of said part.

* * * * *